US006846313B1

(12) United States Patent
Rogers et al.

(10) Patent No.: US 6,846,313 B1
(45) Date of Patent: Jan. 25, 2005

(54) ONE-PIECE BIOCOMPATIBLE ABSORBABLE RIVET AND PIN FOR USE IN SURGICAL PROCEDURES

(75) Inventors: Laurel L. Rogers, N. Attleboro, MA (US); Mariann Sayer, Seattle, WA (US); David W. Overaker, Annandale, NJ (US); Shawn T. Huxel, Lakehurst, NJ (US); Kevin Cooper, Warren, NJ (US); Dennis D. Jamiolkowski, Long Valley, NJ (US); Joseph R. Thomas, Loveland, OH (US)

(73) Assignee: Codman & Shurtleff, Inc., Raynham, MA (US)

( * ) Notice: Subject to any disclaimer, the term of this patent is extended or adjusted under 35 U.S.C. 154(b) by 603 days.

(21) Appl. No.: 09/667,729

(22) Filed: Sep. 22, 2000

Related U.S. Application Data (63) Continuation of application No. 09/185,051, filed on Nov. 3, 1998, now Pat. No. 6,241,732.

(51) Int. Cl.$^7$ ............................................. A61B 17/56
(52) U.S. Cl. ............................. 606/72; 606/76; 606/77; 411/41
(58) Field of Search ............................ 606/72, 73, 75, 606/76, 77, 151; 411/2, 5, 16, 39, 40, 41, 47, 48

(56) References Cited

U.S. PATENT DOCUMENTS

| | | | |
|---|---|---|---|
| 2,402,287 A | 6/1946 | Kearns | |
| 2,941,439 A | 6/1960 | Rapata | |
| 2,956,468 A | 10/1960 | Macy | |
| 3,232,161 A | 2/1966 | Fernberg | |
| 3,411,397 A | * 11/1968 | Birmingham | ................. 411/40 |
| 3,417,438 A | 12/1968 | Schuplin | |
| 3,595,506 A | * 7/1971 | Saunders | ..................... 411/41 |
| 3,765,295 A | 10/1973 | Ptak | |
| 4,011,602 A | 3/1977 | Rybicki et al. | |
| 4,083,289 A | * 4/1978 | Erickson | ..................... 411/16 |
| 4,276,806 A | 7/1981 | Morel | |
| 4,309,137 A | 1/1982 | Tanaka et al. | |
| 4,312,614 A | 1/1982 | Palmer et al. | |
| 4,375,342 A | 3/1983 | Wollar et al. | |
| 4,405,272 A | 9/1983 | Wollar | |
| 4,414,967 A | 11/1983 | Shapiro | |
| 4,519,735 A | 5/1985 | Mächtle | |
| 4,571,134 A | 2/1986 | Beglinger et al. | |
| 4,590,928 A | 5/1986 | Hunt et al. | |

(List continued on next page.)

FOREIGN PATENT DOCUMENTS

| | | |
|---|---|---|
| EP | 0611557 A2 | 8/1994 |
| GB | 2 244 776 A | 12/1991 |

OTHER PUBLICATIONS

Philajämaki, H. et al., "Biodegradable Expansion Plug for the Fixation of Fractures of the Medical Malleolus," *Annales Chirurgiae et Gynaecologiae*, (1994) 83: 49–54.

*Primary Examiner*—Julian W. Woo
(74) *Attorney, Agent, or Firm*—Nutter McClennen & Fish LLP (57) ABSTRACT

A bioabsorbable rivet and pin fastener is formed as an elongated unit that may be used for anchoring, or for attachment of a fixation plate. The rivet has a head mechanically connected to two or more legs that extend generally distally from the head and may flex outwardly from a central rivet axis. The pin is integral with the rivet and oriented along the central axis by a connection such as a web or a plurality of braces, forming an integral, aligned, one-piece assembly that may, for example, be molded as a single piece. The connection breaks under force as the pin is driven into the rivet, so that the pin contacts internal surfaces of the legs and pushes the legs outward into frictional engagement with the surrounding bone. The one-piece assembly may be formed in a gated mold having a central pin with a relief passage that defines the braces between upper and lower portions of the rivet. The braces so formed at the weld line readily part from the mold, and are easily sheared when the pin is advanced during installation of the rivet.

23 Claims, 6 Drawing Sheets

U.S. PATENT DOCUMENTS

| | | |
|---|---|---|
| 4,738,255 A | 4/1988 | Goble et al. |
| 4,759,670 A | 7/1988 | Linder et al. |
| 4,830,556 A | 5/1989 | Nelson |
| 4,834,752 A * | 5/1989 | Van Kampen ............ 623/13.14 |
| 4,856,950 A | 8/1989 | Bushnell |
| 4,901,712 A | 2/1990 | Voegell et al. |
| 4,923,471 A | 5/1990 | Morgan |
| 4,959,065 A | 9/1990 | Arnett et al. |
| 4,976,715 A | 12/1990 | Bays et al. |
| 5,028,187 A | 7/1991 | Sato |
| D320,414 S | 10/1991 | Morgan |
| 5,059,206 A | 10/1991 | Winters |
| 5,102,421 A | 4/1992 | Anspach, Jr. |
| 5,104,394 A | 4/1992 | Knoepfler |
| 5,167,665 A | 12/1992 | McKinney |
| 5,236,438 A | 8/1993 | Wilk |
| 5,268,001 A | 12/1993 | Nicholson et al. |
| 5,282,807 A | 2/1994 | Knoepfler |
| 5,286,152 A | 2/1994 | Anderson |
| 5,290,281 A | 3/1994 | Tschakaloff |
| 5,314,989 A | 5/1994 | Kennedy et al. |
| 5,326,205 A | 7/1994 | Anspach, Jr. et al. |
| 5,398,861 A | 3/1995 | Green |
| D366,114 S | 1/1996 | Ohata |
| 5,480,403 A | 1/1996 | Lee et al. |
| 5,489,210 A | 2/1996 | Hanosh |
| 5,501,695 A | 3/1996 | Anspach, Jr. et al. |
| D369,659 S | 5/1996 | Ohata |
| D370,697 S | 6/1996 | Morgan |
| 5,601,558 A | 2/1997 | Torrie et al. |
| 5,628,579 A | 5/1997 | Forster |
| D381,080 S | 7/1997 | Ohata |
| 5,643,321 A | 7/1997 | McDevitt |
| 5,649,963 A | 7/1997 | McDevitt |
| 5,667,513 A | 9/1997 | Torrie et al. |
| 5,713,903 A | 2/1998 | Sander et al. |
| 5,720,753 A | 2/1998 | Sander et al. |
| 5,725,529 A | 3/1998 | Nicholson et al. |
| 5,741,268 A | 4/1998 | Schutz |
| D395,138 S | 6/1998 | Ohata |
| 5,759,002 A | 6/1998 | Essenberg |
| 5,775,860 A | 7/1998 | Meyer |
| 5,782,865 A | 7/1998 | Grotz |
| 5,797,963 A | 8/1998 | McDevitt |
| 5,814,071 A | 9/1998 | McDevitt et al. |
| 5,911,721 A | 6/1999 | Nicholson et al. |
| 5,928,244 A | 7/1999 | Tovey et al. |
| 5,968,044 A | 10/1999 | Nicholson et al. |
| 6,077,266 A | 6/2000 | Medoff |
| 6,080,161 A | 6/2000 | Eaves, III et al. |
| 6,221,107 B1 * | 4/2001 | Steiner et al. ............ 623/13.14 |

* cited by examiner

ONE-PIECE BIOCOMPATIBLE ABSORBABLE RIVET AND PIN FOR USE IN SURGICAL PROCEDURES

REFERENCE TO RELATED APPLICATION

This application is a con of U.S. patent application Ser. No. 09/185,051 filed on Nov. 3, 1998, now U.S. Pat. No. 6,241,732.

FIELD OF THE INVENTION

The field of art to which this invention relates is surgical devices, in particular absorbable orthopaedic fasteners. Specifically, absorbable polymer rivets and pins for use in the fixation of bone, especially hard tissue of the cranium or face, for plastic or reconstructive surgical procedures.

BACKGROUND OF THE INVENTION

There are currently a variety of metallic fasteners available for attaching bone plates to fracture and surgery repair sites; spinal, cranial, and maxillo-facial plates have all been fastened using metal screws. The disadvantage of metal devices is that they are permanent and may need to be removed through a second surgical procedure. If they remain in the body, tissue atrophy and subsequent loosening of the device may occur.

Synthetic absorbable biocompatible polymers are well known in the art. Such polymers are typically used to manufacture medical devices, which are implanted in body tissue and absorb over time. Synthetic absorbable biocompatible aliphatic polyesters include homopolymers, copolymers (random, block, segmented and graft) of monomers such as glycolic acid, glycolide, lactic acid, lactide(d, l, meso and mixtures thereof), ε-caprolactone, trimethylene carbonate and p-dioxanone. Numerous U.S. patents describe these polymers including U.S. Pat Nos. 5,431,679; 5,403,347; 5,314,989; 5,431,679; 5,403,347; and 5,502,159.

With the advent of absorbable polymers has come a new generation of fasteners (screws, pins, etc.) that are designed to be gradually absorbed by the body as their functional use declines. Devices made of an absorbable material have the advantage that they remain only for the period of time required for healing.

There are a number of orthopaedic rivets disclosed in the prior art.

U.S. Pat. No. 5,167,665 describes a blind rivet with a head on its proximal end and a center mandrel which has a bead or head distal to the head of the rivet. The combination is inserted into a predrilled hole in the bone and is secured under the cortical layer of bone by pulling the center mandrel proximally, thereby collapsing the bead to form a second head that remains under the cortical layer.

U.S. Pat. Nos. 5,268,001 and 5,725,529 describe a flexible sleeve member and an elongated element where the elongated element has an outer diameter that is greater than the inner diameter of the sleeve. The sleeve is inserted into a predrilled hole in the bone. Then the element is inserted into the sleeve forcing it outwardly to secure it to the bone.

U.S. Pat. Nos. 5,326,205 and 5,501,695 describe a fastener adapted to expand into bone. The fastener has a tubular body with a longitudinal opening with a head proximally and members that extend along its body distally. A puller with a head at its distal end is inserted into the tubular body. The assembly is inserted into a predrilled hole in the bone. When the puller is moved proximally, it compresses the members on the tubular body, crimping them so that the members engage the bone. The puller is then broken off at the head of the tubular body, leaving the device secured in the bone.

U.S. Pat. No. 5,480,403 describes a suture anchor that includes a rivet that has radially flexible legs proximally and a setting pin with a sharp tip on its end distal to the flexible legs of the rivet and a suture tied to its proximal end. The rivet and pin are inserted into a predrilled hole. The hole is drilled deeper than the depth of the rivet/pin to accommodate the pin since the pin is initially inserted beyond the distal end of the rivet. The pin is then pulled proximally, expanding the proximal legs of rivet which then engage the bone.

In another embodiment of U.S. Pat. No. 5,480,403, the suture anchor has a rivet and pin where the rivet has legs that extend distally. The rivet and pin are inserted into a predrilled hole. When the pin is pulled proximally, the rivet legs, being tapered such that the inner diameter of the rivet is lass as one moves proximally towards the head of the rivet, radically expand to secure the suture anchor to the bone surface as the pin is pulled proximally.

U.S. Pat. Nos. 5,713,903 and 5,720,753 describe a fastener having expanded legs at its distal end and a pin with a flared distal end set in a central bore at a depth greater than the length of the fastener legs. When the pin is moved proximally, the flared end of the pin expands the legs of the fastener to secure it to the bone. The pin is then detached at a notch at the head of the fastener. This fastener is specifically for securing soft tissue to bone.

These patents relate to devices which are inserted into a hole and then deployed by driving a member upwards, or proximally, through or into a radially flexible portion of the device. This requires that the hole be deeper than the depth of the deployed device in order to leave enough room to fully insert the device before deployment. Such designs are undesirable for surgical applications where only a thin layer of bone is available for attachment or it is not possible to drill beyond the depth of the thin bone layer for fear of damaging underlying soft tissues, such as in cranial and maxillo-facial surgical procedures. In such cases, the required length of the fastener for adequate fastening strength is very close to the total thickness of the bone.

U.S. Pat. No. 4,590,928 describes an anchor consisting of an elongated cylindrical body with a tapered coaxial channel and radially flexible legs and a pin insertable into the end having the head, the proximal end. The body is placed into a hole formed in bone and the pin is inserted into the channel to expand the legs radially outward into the surrounding bone. The body and pin are of biocompatible material and the body contains carbon fibers embedded in and extending longitudinally along its interior. Since carbon fibers are not absorbed by or resorbed within the body, this fastener is only partially absorbable.

This patent, U.S. Pat. No. 4,590,928, describes a fastener having a solid pin. It is well known that the material properties, such as Young's modulus of elasticity and the material yield stress, of bone tissue change significantly with age and vary significantly among individuals of the same age and sex. Having a solid pin therefore limits the fastening ability of the device since the pin cannot deform if the surround ing bone is so stiff that the legs cannot expand radially outwards.

In such a case where the surrounding bone is stiffer than that for which the device was designed and the pin is solid, the large force required to drive the rigid pin into the tapered hole will be such that either the legs will be deformed and rendered useless or the pin will be crushed.

A number of the above described rivet constructions require specialized tooling for their proper installation, and this may involve two separate tools, or a single tool of relatively complicated construction. Thus, for example, a rivet system may require separate cylindrical or rod-like tools for inserting the outer rivet body, and driving or threading in a central expander pin, respectively. In dealing with the several cooperating parts of the rivet, there is a risk of separation of the components within their packaging prior to use, of dropping one or more components in the surgical wound, or of mis-handling or mis-aligning a component due to the small size of the individual parts. Further, the multi-component nature of such rivet structures may necessitate installation tooling that is ill adapted for, or incapable of operating to, install plural rivets before requiring reloading.

Accordingly, it would be desirable to provide a biologically absorbable rivet assembly that is easily installed.

It would also be desirable to provide a biologically absorbable rivet assembly that may be loaded in an installation tool to permit placement of multiple rivets before reloading.

It would also be desirable to provide a biologically absorbable rivet assembly with enhanced handling and shipping integrity.

SUMMARY OF THE INVENTION

The invention disclosed is a biocompatible bioabsorbable rivet and pin fastener that, in one aspect comprises:

(1) a biocompatible rivet having a head with a proximal end and a distal end and a central axis, the head having an internal passage extending from the proximal to the distal end of the head that is substantially parallel to the central axis of the head, the distal end of the head being mechanically connected to two or more legs that extend generally distally from the head and have an internal surface that faces the central axis, and (2) a biocompatible pin having a radially compressible cross-section that is less compliant than the legs of the rivet which is adapted to be inserted into the internal passage of the rivet and which as advanced from the proximal end toward the distal end of the head of the rivet will contact the internal surface of said legs to apply force on said legs in a direction substantially perpendicular to the central axis.

The pin may include a circumferential notch or rib located on the lateral surface of the pin. The notch or rib on the pin surface would mate with a circumferential rib or notch on the inner surface of the internal channel passing through the body. This would provide a means of locking the pin in position to prevent axial migration of the pin after full insertion of the pin.

The pin may be: 1) a separate element, or 2) an element integral with the body through a breakable connection such that the downward driving force would detach the pin from the body and then drive the pin distally into the body.

The pin may have flexible members, which are less compliant, or stiffer, than the flexible legs of the body. The pin will therefore be stiff enough to expand the legs of the body radially outwards when the device is deployed in bone with average material properties, for which the device would be designed, but also will have enough compliance to flex inwards when the device is deployed in very stiff bone in which the legs of the body cannot expand outwards.

The invention includes in another aspect a biocompatible bioabsorbable rivet and pin fastener having (1) a biocompatible rivet portion including a head with a proximal end, a distal end and a central axis, the head having an internal passage extending from the proximal to the distal end of the head that is substantially parallel to the central axis of the head, the distal end of the head being mechanically connected to two or more legs that extend generally distally from the head and have an internal surface that faces the central axis, and (2) a biocompatible pin having a radial cross-section that, when inserted into the internal passage of the rivet and advanced from the proximal end toward the distal end of the head of the rivet contacts the internal surface of said legs to force the legs in a direction outwardly from the central axis, wherein the pin is integrally connected with the body by a breakable connection such that the rivet and pin form an elongated single piece assembly for shipping and handling; and driving force directed along the central axis breaks the connection and drives the pin distally into the body to fix the fastener in place. The rivet and pin assembly preferably forms a single coaxial unit of enhanced length that is easily handled, and may be loaded in a driver for convenient installation.

The foregoing and other features and advantages of the invention will become more apparent from the following description and accompanying examples.

DETAILED DESCRIPTION OF THE INVENTION

Figure 1:
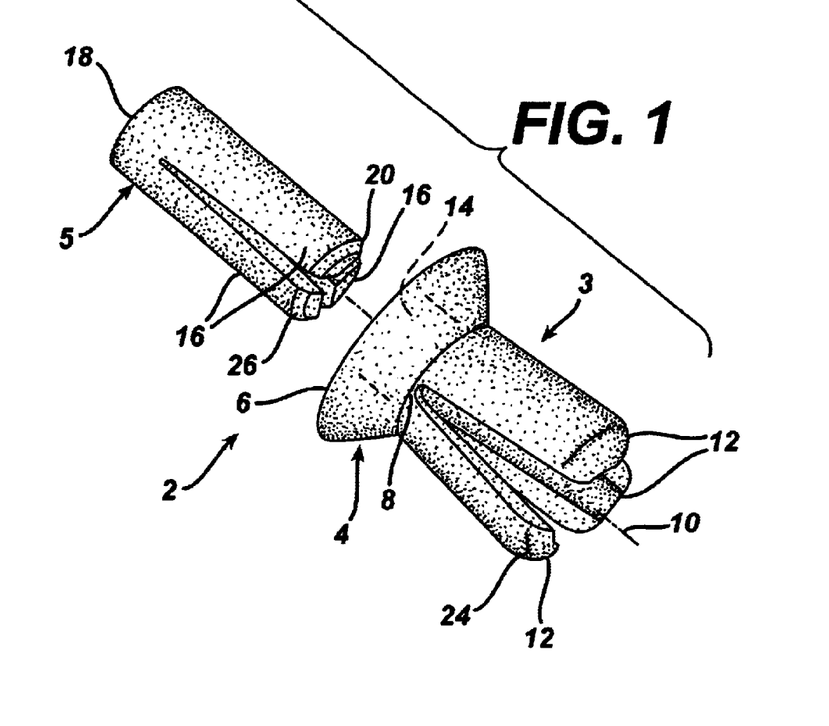
FIG. 1 is a perspective view of one embodiment of the biocompatible, absorbable rivet and pin of the present invention.

One embodiment of the rivet and pin fastener according to a first aspect of the present invention is illustrated in FIG. 1. The rivet and pin fastener 2 is comprised of the rivet 3 and the pin 5. The rivet is made up of the head 4 and at least two legs 12 that are attached to the distal end 8 of the head. The proximal end 6 of the head has an internal passage 14 that is substantially parallel to the central axis of the head 10. The head 4 preferably will expand in diameter from the distal to proximal ends to provide a surface for securing a orthopedic devices to bone upon deployment of said fastener. The pin 5 is radially compressible, which means that the cross-sectional diameter of at least a portion of the pin may be reduced if sufficient radial force is applied to the pin. One embodiment of the pin 5 has at least two distal radially flexible members 16 that are jointed together at junction 18. The rivet and pin fastener is deployed by advancing the insertion end of the pin into the internal passage 14 in the proximal end 6 of the rivet 4. The insertion end 20 of the pin is then advanced toward the distal end 8 of the head 4. As the pin 5 is advanced, the insertion end 20 of the pin will contact the legs 12 of the rivet and exert a force generally perpendicular to the central axis 10 of the rivet 4. The flexible members 16 of the pin 5 are designed to flex rather than cause the flexible legs 12 of the rivet 4 to break or separate from the head 4 as the legs expand outwards to frictionally engage with the adjacent bone.

The flexible legs 12 in the rivet preferably have a geometry, such that the legs 12 increase in thickness extending distally from the connection to the head 4. This feature enables the legs 3 to be forcibly expanded outwards when the straight pin 5 is driven into the internal passage 14. In such a case where the legs 12 increase in thickness extending distally from the connection to the head, the fastener has enhanced anchoring properties when deployed because the outside diameter of the rivet at the distal portion of the legs 12 is larger than the outside diameter of the rivet at the distal end of the head where the legs 12 attach. The legs 12 are therefore expanded outwards beyond the initial hole diameter created in the dense surface layer of bone, the cortex. The legs 12 may also have a chamfered or rounded leading edge 24 to improve the ease of insertion of body into a hole. Likewise, the pin 5 may have a chamfered or rounded leading edge 26 to improve ease of insertion of the pin 5 into the internal passage 14 in the rivet 4. The rivet may also have a chamfered inner surface to allow removal of the device, if necessary, with an applier after it has been set in place.

The pin 5 has radially flexible members 16 at its distal end. In accordance with one aspect of the invention, the flexible members 16 of the pin 5 are less compliant, or stiffer, than the flexible legs 12 of the rivet 4. This results in a pin 5 with less structural compliance, or greater structural stiffness, than that of the rivet 4 at the distal end of the device. Insertion of the pin 5 into the internal passage 14 of the rivet 4 will result in radial expansion of the legs 12 of the rivet 4 and radial compression of the members 16 of the pin 5. Since the total stiffness of the members 16 of the pin are greater than the total stiffness of the legs 12 of the rivet 4, the resultant radial force will always be outward to frictionally engage the legs 12 of the rivet 4 with the surrounding bone. However, to prevent the pin 5 from shearing or deforming the legs 12 to the point that the legs will cease to effectively frictionally engage the surrounding bone, at least a portion of the pin 5 will radially compress at a threshold value less that the force which would substantially damage the legs 12.

Figure 2:
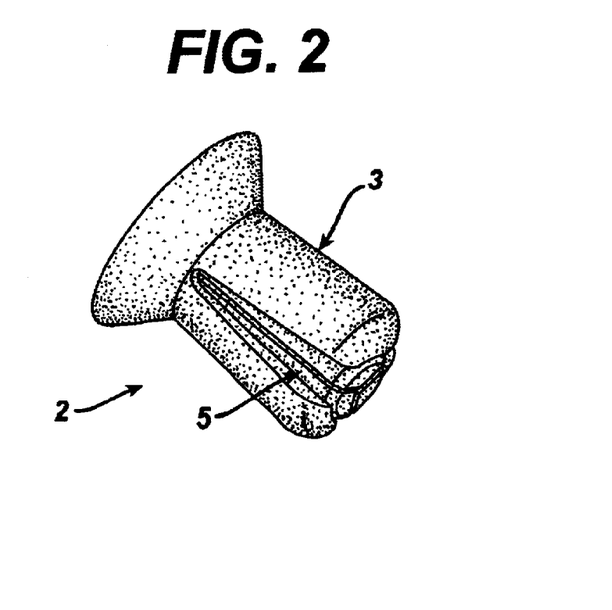
FIG. 2 is a perspective view of the rivet with the pin inserted into the internal passage of the head.

In another embodiment of the present invention, the surface 28 of the passage 14 has a circumferential notch 30 which mates with a circumferential rib 32 on the lateral surface 31 of the pin 5. Conversely, in another embodiment of the present invention, the surface of the channel 28 may have a circumferential rib which mates with a circumferential notch on the lateral surface of the pin 5. Both embodiments provide a locking means for the inserted pin to prevent axial migration of the pin after insertion. Additionally, this embodiment can easily provide a tactile and/or audio feedback to alert the surgeon that the pin has been locked into place in the rivet.

Figure 3:
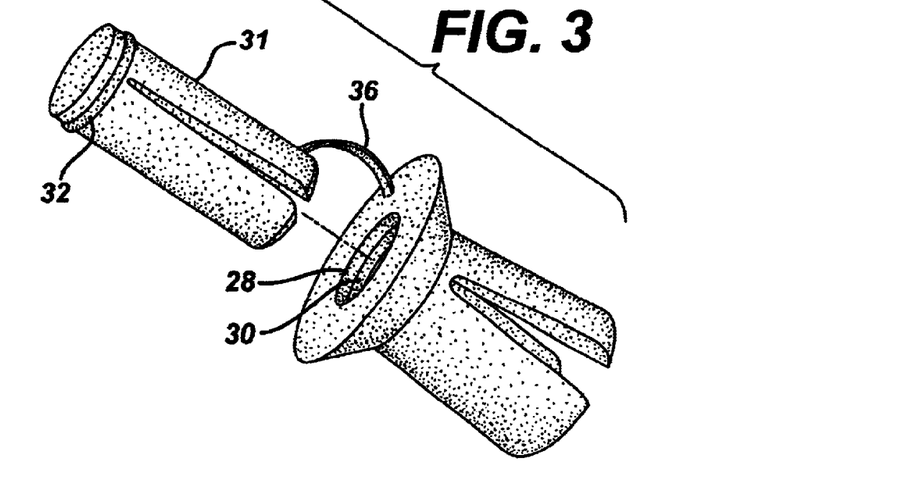
FIG. 3 is a perspective view of an alternative embodiment of the present invention as a one-piece unit, and wherein a locking mechanism is present.

In another embodiment of the present invention illustrated in FIG. 3, the rivet 4 and the pin 5 are attached by a thin material connection 36 within the head 4 to form a one-piece device. Once the device is inserted into a hole in bone, a driving force applied to the pin suffices to break the material connection and then drive the pin into the body to deploy the fastener.

Figure 4:
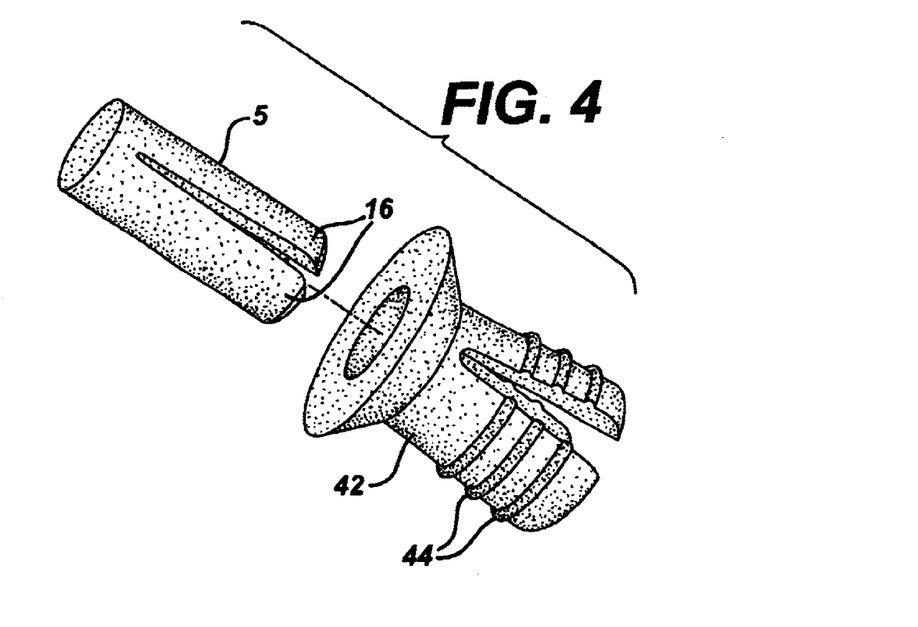
FIG. 4 is a perspective view of another alternative embodiment of the present invention wherein ribs are provided on the legs of the rivet to insure engagement of the rivet with surrounding tissue when it is deployed.

In another embodiment of the present invention illustrated in FIG. 4, the outside lateral surfaces 42 of the legs 12 have one or a number of ribs 44 and/or protrusions that embed into the adjacent bone upon deployment of the fastener in order to increase the fastening strength of the device.

Figure 5:
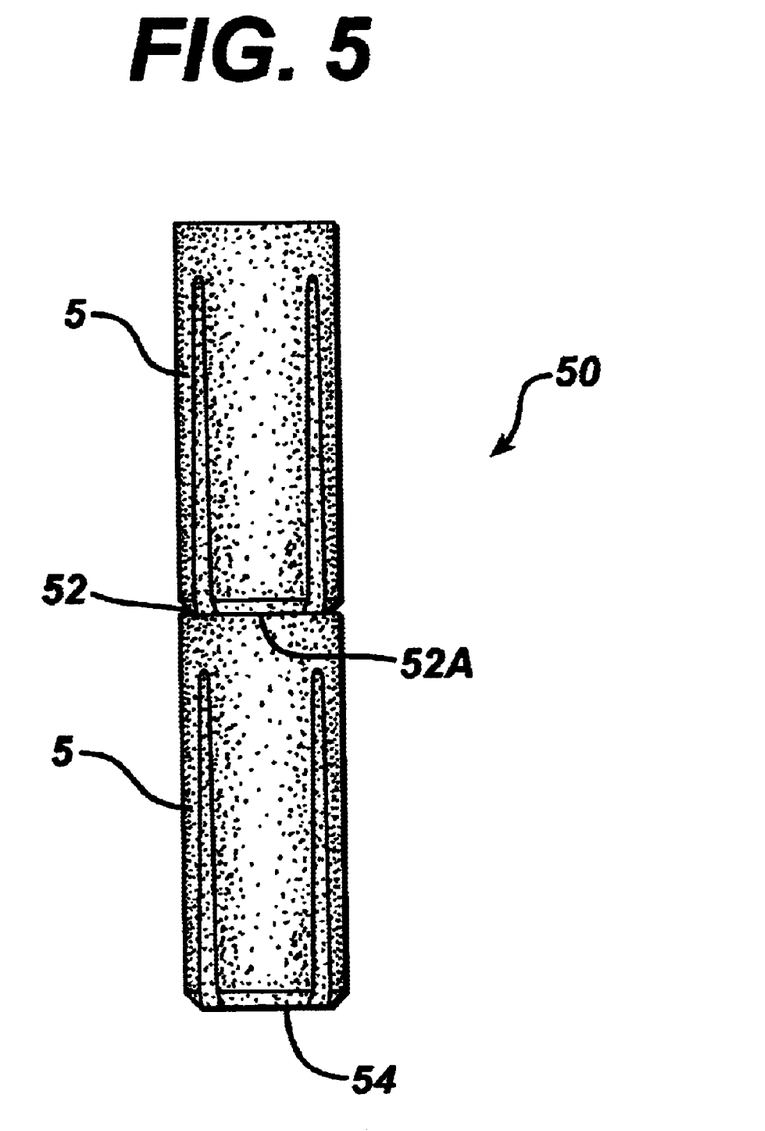
FIG. 5 is a perspective view of an alternative embodiment of the pin for the embodiments of FIGS. 1–2 and 4.

In another embodiment of the present invention illustrated in FIG. 5, the pin 5 could be part of a continuous rod 50 of pins 5, which are separated by the round or chamfer 52 on the leading edge of the pin 5. A driving force would be applied to the continuous rod 50 to drive the distal end of the rod 54 into the rivet 4 until the insertion end of the pin 5 is fully engaged with the rivet 4. The distal pin is then detached from the rod 50 to break the connection 52 by applying sufficient bending force to the rod or by cutting at the connection 52 thereby generating a new distal end 52A. The continuous rod would therefore be used to deploy a number of rivets.

Figure 6:
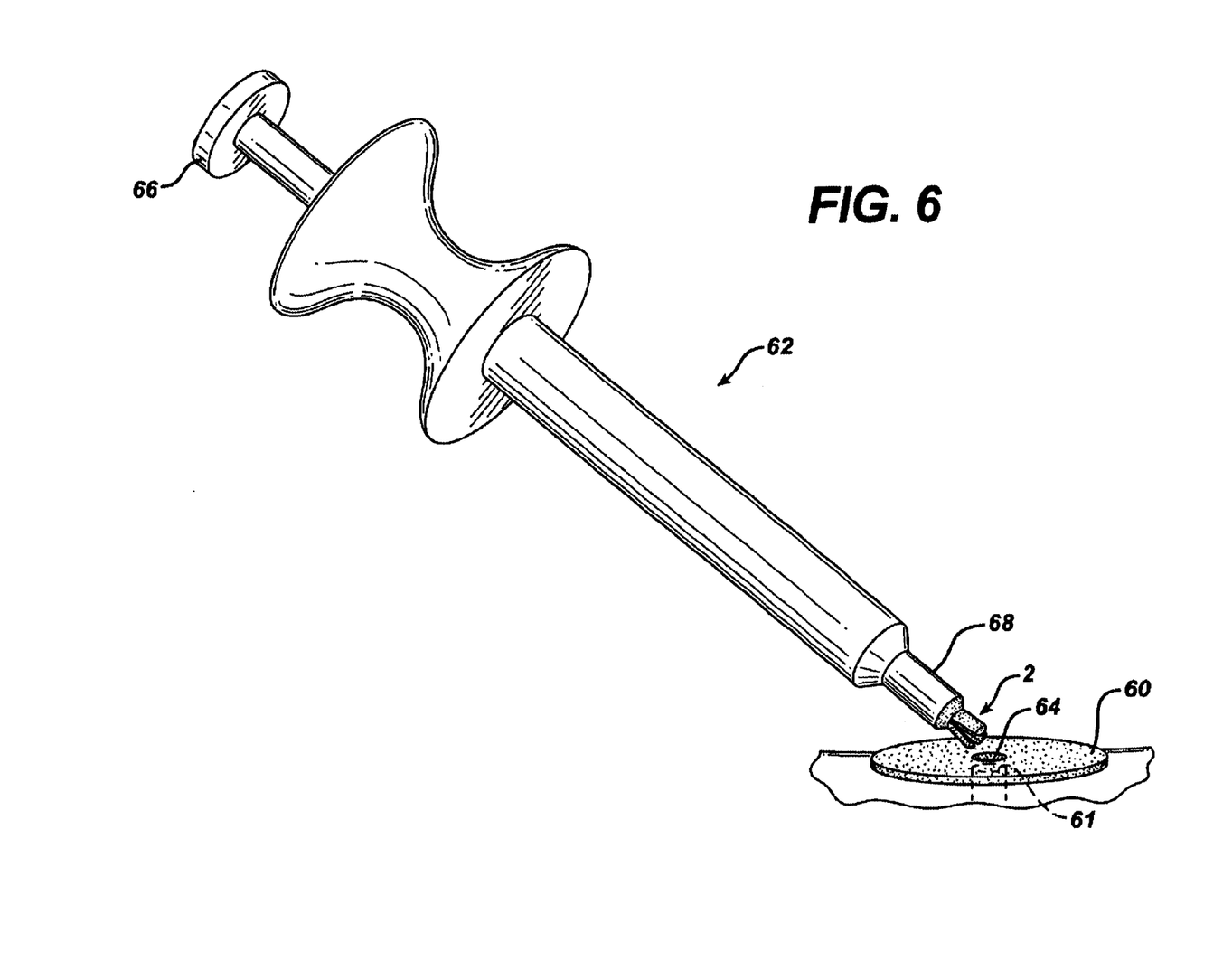
FIG. 6 is a perspective view of an applier for the rivet and pin fastener.

Also disclosed is a method of applying the fastener 2 as shown in FIG. 6. After the surgeon has drilled a hole 61 in the bone at the location where a plate 60 or other device will be fastened, the rivet and pin are loaded in applier 62. The rivet 4 is then inserted through the plate hole 64 into hole 61. The pin 5 is driven into the rivet 4 by applying a downward force on the plunger 66 of the applier 62. The process is repeated as needed until adequate holding power is obtained for the plate 60.

Suitable materials from which the fastener may be formed include biocompatible polymer selected from the group consisting of: aliphatic polyesters; polyorthoesters; polyanhydrides; polycarbonates; polyurethanes; polyamides; polyalkylene oxides; and combinations thereof. The orthopedic fastener of the present invention can also be formed from absorbable glasses or ceramics comprising calcium phosphates and other biocompatible metal oxides (i.e., CaO). The fastener of the present invention can further comprise combinations of absorbable ceramics, glasses and polymers.

In the preferred embodiment, the orthopedic fastener is comprised of aliphatic polymer and copolymer polyesters and blends thereof. The aliphatic polyesters are typically synthesized in a ring opening polymerization. Suitable monomers include but are not limited to lactic acid, lactide (including L-, D-, meso and D,L mixtures), glycolic acid, glycolide, _-caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof. These monomers are generally polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization is typically carried out at a temperature range from about 80°

C. to about 240° C., preferably from about 100° C. to about 220° C., until the desired molecular weight and viscosity are achieved.

The polymer blends of the present invention are manufactured in a conventional manner. One method of blending the homopolymers and copolymers, prepared as described above, is to individually charge the polymers into a conventional mixing vessel or reactor vessel having a conventional mixing device mounted therein, such as an impeller or equivalents thereof. Then, the polymers and copolymers are mixed at a temperature of about 100° C. to about 230° C., more preferably from about 160° C. to about 200° C., for about 5 to about 90 minutes, more preferably for about 10 to about 45 minutes, until a uniformly dispersed polymer blend is obtained. Then, the polymer blend is further processed by removing it from the mixing device, cooling to room temperature, grinding, and drying under pressures below atmospheric at elevated temperatures for a period of time using conventional apparatuses and processes. Another appropriate method of blending the homopolymers or copolymers is by passing the polymers through a twin screw-extruder with an appropriate mixing zone or zones.

Under the above described conditions, the polymers and blends composed of glycolide, _-caprolactone, p-dioxanone, lactide and trimethylene carbonate will typically have a weight average molecular weight of about 20,000 grams per mole to about 300,000 grams per mole, more typically about 40,000 grams per mole to about 260,000 grams per mole, and preferably about 60,000 grams per mole to about 225,000 grams per mole. These molecular weights provide an inherent viscosity between about 0.5 to about 4.0 deciliters per gram (dL/g), more typically about 0.7 to about 3.5 dL/g, and most preferably about 1.0 to about 3.0 dL/g as measured in a 0.1 g/dL solution of hexafluoroisopropanol (HFIP) at 25° C. Also, it should be noted that under the above-described conditions, the residual monomer content would be less than about 5 weight percent.

Articles such as absorbable fastener medical devices of the present invention are molded from the polymers and blends of the present invention by use of various injection and extrusion molding equipment equipped with dry nitrogen atmospheric chamber(s) at temperatures ranging from about 100° C. to about 230° C., more preferably 140° C. to about 200° C., with residence times of about 1 to about 20 minutes, more preferably about 2 to about 10 minutes. The preferred device is an orthopaedic rivet fastener. The preferred device should be molded with the rivet having the legs 12 oriented in the an expanded position (the position that the legs will be expanded to when the pin in place). Molding the rivet with the legs expanded will tend to reduce the stress at the junction of the legs 12 with the head 4 when the legs are expanded. Reducing the stress at this junction should extend the useful life of the rivet and pin fastener after implantation.

In another embodiment of the present rivet invention, the polymers and blends can be used as a drug delivery matrix. To form this matrix, the polymer would be mixed with a therapeutic agent. The variety of different therapeutic agents that can be used in conjunction with the polymers of the present invention is vast. In general, therapeutic agents which may be administered via the pharmaceutical compositions of the invention include, without limitation: antiinfectives such as antibiotics and antiviral agents; analgesics and analgesic combinations; anti-inflammatory agents; hormones such as steroids; bone regenerating growth factors; and naturally derived or genetically engineered proteins, polysaccharides, glycoproteins, or lipoproteins.

Matrix formulations may be formulated by mixing one or more therapeutic agents with the polymer. The therapeutic agent, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001% to about 70%, more typically about 0.001% to about 50%, most typically about 0.001% to about 20% by weight of the matrix. The quantity and type of polymer incorporated into the drug delivery matrix will vary depending on the release profile desired and the amount of drug employed.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like.

Following this or similar procedures, those skilled in the art will be able to prepare a variety of formulations.

In another embodiment of the present rivet invention, a biocompatible dye could be added to the polymer comprising the device during processing in order to make it more visible in the surgical field. Alternatively, the pin and rivet could be color coded to provide a visual feedback to alert the surgeon that the pin has been inserted into the rivet. The rivet and pin combination may also incorporate tactile and/or audio feedback to alert the surgeon that the device has been inserted.

Additionally, radio-opaque markers may be added to the rivet or pin to allow imaging of the rivet and pin fastener after implantation.

The following non-limiting examples are illustrative of the principles and practice of this invention. Numerous additional embodiments within the scope and spirit of the invention will become apparent to those skilled in the art.

EXAMPLES

The examples describe a fastener system that is fabricated from an absorbable polymer or polymer blends and consists of a body with flexible legs and a pin that is inserted into the body to expand the legs.

In the synthetic process, the high molecular weight aliphatic polyesters of the device of the present invention are prepared by a method consisting of reacting lactone monomers via a ring opening polymerization at temperatures of 100° C. to 230° C. for 2 to 24 hours under an inert nitrogen atmosphere until the desired molecular weight and viscosity are achieved.

The polymer blends of the present invention are prepared by individually charging the synthesized aliphatic homo- and co-polyesters into a conventional mixing vessel. The homopolymers and copolymers are mixed at a temperature of 100° C. to 230° C., for 5 to 90 minutes until a uniformly dispersed polymer blend is obtained.

In the examples which follow, the blends, polymers and monomers were characterized for chemical composition and purity (NMR, FT-IR), thermal analysis (DSC), melt rheology (melt stability and viscosity), molecular weight (inherent viscosity), and baseline mechanical properties (stress/strain).

Inherent viscosities (I.V., dL/g) of the blends and polymers were measured using a 50 bore Cannon-Ubbelhode dilution viscometer immersed in a thermostatically controlled water bath at 25° C. utilizing chloroform or HFIP as the solvent at a concentration of 0.1 g/dL.

Several examples will be described in the following few pages. Parts and percentages where used are parts and percentages as specified as weight or moles.

Example 1

Synthesis of a 85:15 (mol/mol) oly(lactide-co-glycolide) Copolymer

The method described below and utilized in this example is similar to those described in U.S. Pat. Nos. 4,643,191, 4,653,497, 5,007,923, 5,047,048 which are incorporated by reference, and is known to those skilled in the art.

To a flame dried 500 mL 1-neck round bottom flask equipped with an overhead mechanical stirrer and nitrogen inlet, 268 grams (1.86 moles) of L(-) lactide, 38.4 grams (0.330 moles) of glycolide, 0.53 grams ($7 \times 10^{-3}$ moles) of glycolic acid initiator, and 131 microliters of a 0.33 M solution of stannous octoate catalyst are added.

The assembly is then placed in a high temperature oil bath at 185° C. The stirred monomers quickly begin to melt. The low viscosity melt quickly increases in viscosity. Mechanical stirring of the high viscosity melt is continued for a total reaction time of 4 hours.

The 85:15 (mol/mol) poly(lactide-co-glycolide) copolymer is removed from the bath, cooled to room temperature under a stream of nitrogen, isolated and ground. The polymer is then dried under vacuum at 110° C. for 24 hours to remove unreacted monomer. Inherent viscosity using HFIP as a solvent is 1.90 dL/g.

Example 2

Injection Molding a Rivet and Pin of an 85:15 poly (lactide-co-glycolide) Copolymer 1.5 Kg of the copolymer as formed in Example 1 is added to a nitrogen purged hopper of a 28 ton Engel injection molder equipped with an 18 mm diameter barrel to form a rivet or pin as shown in FIG. 1. Three heating zones of 200, 190, and 185° C. are employed to melt the polymer as it entered the barrel. A nozzle temperature of 185° C. with an injection pressure of 700 psi and a speed of 2 in/s is used to feed the molten material down the barrel. Each injection will produce a single part in a single cavity mold. A temperature of 45° C. is used in the mold to optimize the stress levels in the part. Using this process two parts are formed per minute.

Example 3

Step-by-Step Process of Fastener Use in Animal Model or for Human Use

Referring to FIG. 6, after the surgeon has drilled a hole 61 in the bone location where a plate 60 or other device must be fastened, the rivet 4 and pin 5 are loaded into the receiver 68 of the applier 62. The rivet 4 is then inserted into the plate hole 64 and the pin 5 is driven into the rivet 4 by applying a downward force on the plunger 66 of the applier 62. The size of the hole the surgeon drills should be modified based on the type of bone and the cross-sectional diameter of the rivet (with the pin in place). The hole that will be drilled in the bone will necessarily be smaller than the diameter of the rivet with the pin in place. However for bone which is of a soft nature (substantially cancellous bone), the hole diameter may be even smaller to increase the frictional engagement of the rivet and pin fastener with the softer bone. For bone which is harder in nature (substantially cortical bone), the hole diameter should be closer to the diameter of the rivet (with the pin in place) to ease the application of the rivet and pin fastener.

In accordance with another aspect of the present invention, the rivet and pin may be formed together as a single unit. Preferred embodiments of this aspect of the invention result in a larger fastener assembly that is more easily handled by the surgeon, wherein components do not become separated or lost during packaging, shipping, handling or installation, and wherein the single-piece rivet enjoys a compact form that allows implementation of convenient and effective installation tooling for more efficient effective surgical use.

Figure 3A:
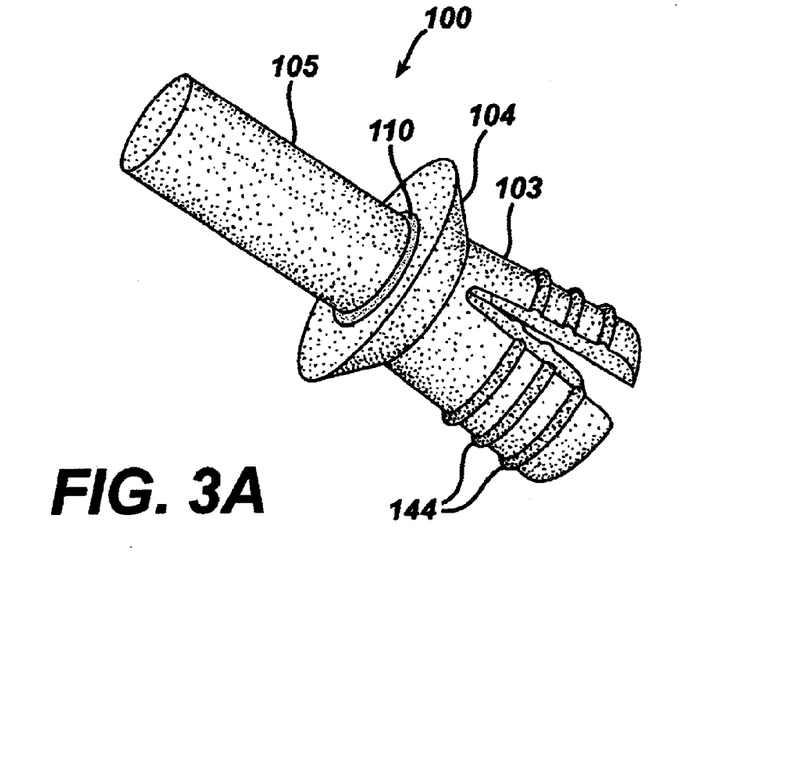
FIG. 3A is a perspective view of another embodiment of the present invention as a one-piece unit, and wherein a breakable web interconnects the pin and rivet portions.

FIG. 3A illustrates one embodiment 100 of a single piece rivet according to this aspect of the invention. As shown, the single piece rivet includes a pin portion 105 and a rivet portion 103 connected together as a rigid unit by a connecting web 110 that extends circumferentially around the pin near its distal tip and connects to the head 104 of the rivet 103. The rivet 103 may be shaped substantially like the rivet of any of the foregoing embodiments with an enlarged head 104 and dependent legs 112. The illustrated embodiment includes gripping ridges 144 on the legs for engagement with surrounding tissue. The pin 105 may be generally of cylindrical form as illustrated, and preferably has a beveled or chamfered leading edge at its distal end (not visible, below the diaphragm) similar to chamfer 26 of the embodiment of FIG. 1, to assure smooth entry when the pin 105 is driven into the rivet 103. The web 110 is formed of the same material as the pin 105 and the rivet 103. Web 110 may, for example, have a thickness in the range of one to ten mils, and preferable about two to five mils, forming a breakable connection between the pin and the head of the rivet that holds the pin in alignment, but shears when the pin is driven forward into the body of the rivet. The entire one-piece assembly may be formed, for example, by injection molding in a gated mold having a central core pin in the lower portion corresponding to shape of the central opening through the rivet body. The core pin has a top surface against which the web 110 and leading edge of the pin 105 are formed.

Figure 3B:
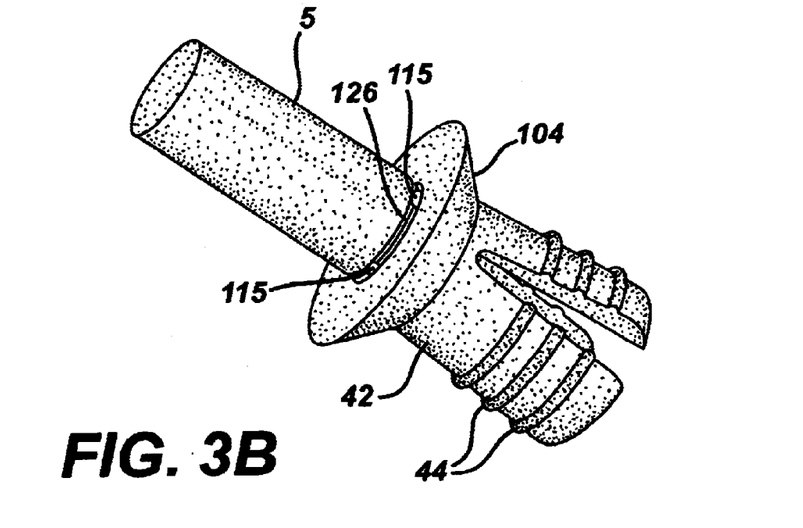
FIG. 3B is a perspective view of yet another embodiment of the present invention as a one-piece unit, and wherein a plurality of braces interconnect the pin and rivet portions.

FIG. 3B illustrates another embodiment of a single-piece rivet in accordance with this aspect of the invention, wherein the web 110 is replaced by a plurality of braces 115. Each brace extends from the bevel 126 or from the central portion of the distal end of the pin, to a portion of the rivet head 104 that may for example be recessed below the surface of the rivet. Thus, the braces 115 extend obliquely and centrally inward between the rivet and the pin. Preferably, the braces are arranged symmetrically, e.g., as two diametrically opposite braces, or as a set of three or four braces equispaced around the parameter of the pin. This assures that the body of the pin 105 remains coaxial and centered with respect to the body of the rivet 103, so that when force is applied to the pin it enters the central passage in the rivet smoothly without jamming. The small isolated braces shear easily and their internal positioning assures that they are captured within the rivet and wound opening, so that riveting produces minimal debris or scattering.

As seen in FIGS. 3A and 3B, the one-piece rivet/pin article of the invention has a length that is essentially twice the length of the rivet body or the pin alone, and unlike the tethered embodiment of FIG. 3 has a shape which is both fixed, and geometrically simple. This results in enhanced handling characteristics so that a surgeon may more conveniently pick up, hold and manipulate the rivet, as well as enhanced mechanical handling properties. For example, the overall shape is well adapted to be installed by a suitably designed installation tool which accepts rivets in bulk, or rivets preloaded in aligned cartridges, magazines or strip holders, and inserts and expands the rivet in a single operation. Thus, the rivet of FIGS. 3A and 3B may achieve the ease of use which has long been available for items such as surgical staples or clips.

Figure 7:
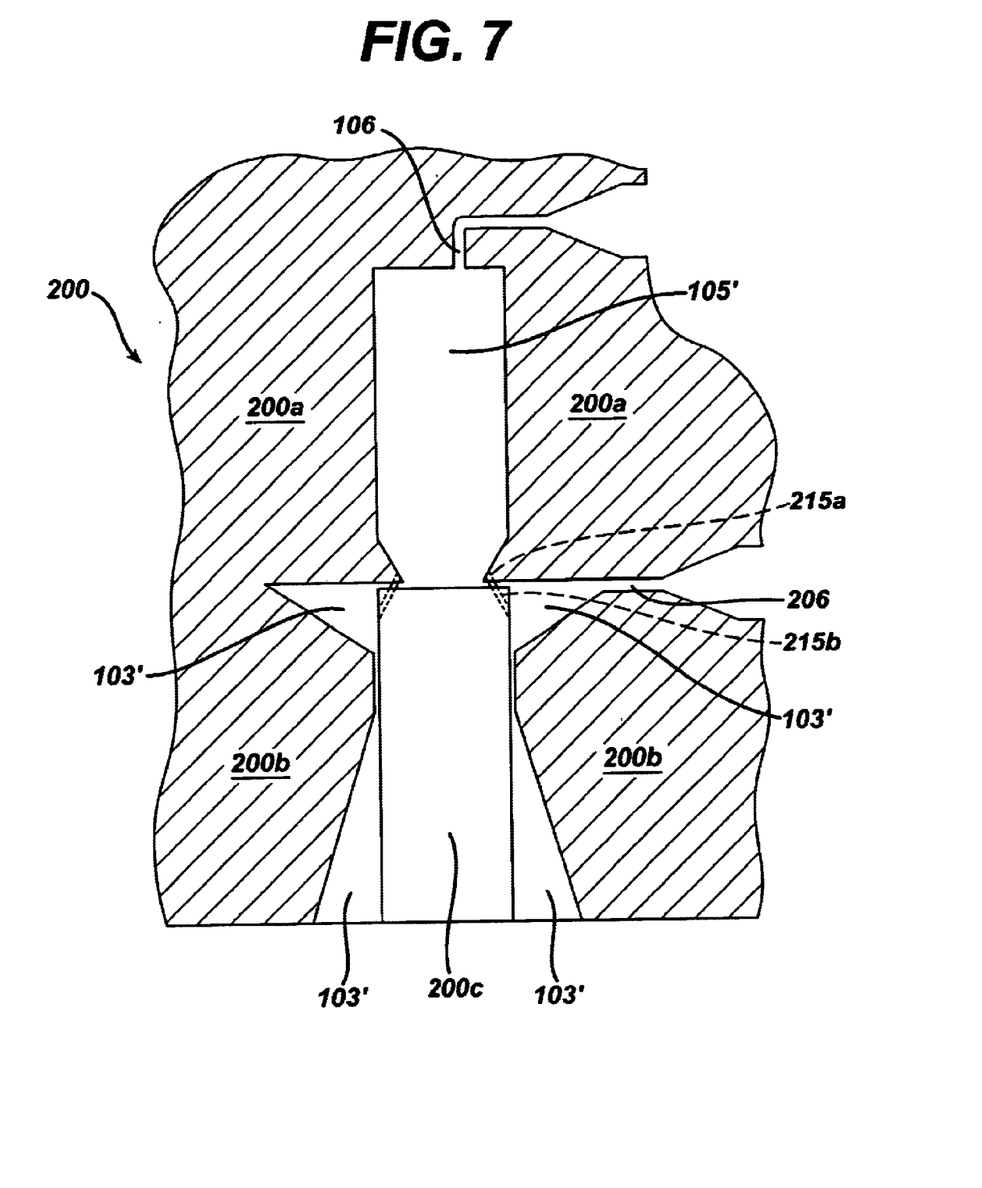
FIG. 7 illustrates a mold for forming the rivet of FIG. 3B.

FIG. 7 illustrates a gated mold assembly 200 useful for forming the one-piece rivet of FIG. 3B. As shown, the mold assembly includes a generally upper mold portion 200a and a lower mold portion 200b, with a movable core pin 200c positioned in the lower portion. The upper portion 200a forms the pin 105 in a mold cavity 105' having a gated entrance 106 for the biocompatible polymer. Similarly, the lower portion 200b forms the expansile rivet body 103 in a generally double funnel-shaped mold cavity 103' corresponding to the rivet head and legs of the rivet body. A second polymer inlet gate 206 feeds the lower cavity. Other gates and sprues or runners may be provided as appropriate for the feedstock and part configuration being molded.

FIG. 7 illustrates the mold in cross section, and it will be understood that the cavity 103' and the cavity 105' are each substantially radially symmetric. A core pin 200c extends upward in the lower portion 200b of the mold to define the central opening of the rivet body, so that the polymer fills two generally open-core tapered conical spaces constituting the cavity 103' around the core pin 200c. Further, a plurality of channels 215a in the upper body and 215b in the core pin align with each other to form smaller cross-cavity passages which fill with polymer to mold the braces 115 (FIG. 3B) that interconnect the pin and rivet body. The core pin 200c is preferably formed with a set of radially-protruding fins that segment the surrounding lower mold cavity to form the plural laterally projecting lobes at its lower portion that are the legs of the rivet, while the upper portion corresponds to the shape of the head of the rivet. A separate material gate 206 in the head region of the lower portion assures that adequate polymer pressure and flow are available at the junction region to form the delicate braces 115 of the rivet.

After the rivet is formed the core pin may be withdrawn without fracturing the braces 115. Preferably, the mold 200 is formed as a two-piece mold that separates front and back portions along a symmetrically disposed diametral plane parallel to the plane of the drawing, FIG. 7. Thus, the channels 215a, 215b may lie on the parting line of the two mold halves, and after withdrawal of core pin 200c, the molded rivet unit is removed by separating the front and back portions of the mold. By forming the braces 115 on the weld line between two larger bodies of polymer gated into the mold at separate positions, the brace portions are formed as easily-sheared braces. Sprues may be provided to assure full penetration of the braces channels 215a, 215b. Sprues or runners may also be provided elsewhere in the mold as appropriate for the pressures and materials being used to assure complete filling.

This manner of forming a one-piece article requires a lower number of mold components, and the specific embodiment of FIG. 3B assures that the break-away ties or braces are captured in the wound. The single piece construction allows effective packaging of the rivets in a simple bubble pack configuration without the risk of disassembly, malassembly or component loss.

The invention being thus disclosed and described, further variations and modifications will occur to those skilled in the art and all such variations and modifications are considered to lie within the scope of the invention as described herein and defined by the claims appended hereto and equivalents thereof.

What is claimed is:

1. A surgical rivet and pin fastener device comprising
   a rivet formed of bioabsorbable, biocompatible material, having an elongated body extending along a rivet axis with an enlarged head at a proximal end thereof and a plurality of spreadable legs dependent from said head, the legs being arranged generally circumferentially to define a central opening extending distally along the rivet axis,
   a radially compressible pin formed of said material extending generally proximally of said enlarged head and having radially flexible members extending to a distal end of the pin from a junction at a proximal end thereof, said pin and said legs being sized so that the legs are spread to fix the rivet in position when the pin moves into the central opening, and
   an integral support interconnecting said rivet and said pin so as to position the pin along the rivet axis and generally outside the rivet forming an elongated one-piece assembly for handling and installation, said support breaking upon application of an axially-directed force to for driving the pin into said central opening and fixing the rivet in position.

2. The surgical rivet and pin fastener device of claim 1, wherein said integral support includes a plurality of oblique support braces formed of said material.

3. The surgical rivet and pin fastener device of claim 2, having between two and five support braces.

4. The surgical rivet and pin fastener device of claim 1, wherein said integral support includes a web.

5. The surgical rivet and pin fastener device of claim 1, wherein the device is a molded device configured such that the integral support spans a weld line across gated mold portions so as to constitute a weakened shear connection between the rivet and pin.

6. The surgical rivet and pin fastener device of claim 1, wherein said material is dyed to enhance visibility.

7. The surgical rivet and pin fastener device of claim 1, wherein the rivet contains a therapeutically effective amount of a therapeutic agent.

8. The surgical rivet and pin fastener device of claim 7, wherein the aliphatic polyester is formed from a monomer selected from the group consisting of lactic acid, lactide (including L-, D-, meso and D,L mixtures), glycolic acid, glycolide, ε-caprolactone, p-dioxanone (1,4-dioxan-2-one), trimethylene carbonate, 1,3-dioxan-2-one, p-dioxanone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof.

9. The surgical rivet and pin fastener device of claim 1, wherein the device is made from biocompatible aliphatic polyester.

10. The surgical rivet and pin fastener device of claim 1, wherein the material comprises an aliphatic polyester selected from the group consisting of polylactide, polyglycolide, poly-1,4-dioxan-2-one, polytrimethylene carbonate and poly (ε-caprolactone), copolymers and blends thereof.

11. A bioabsorbable biocompatible rivet and pin fastening device comprising:

(a) a bioabsorbable, biocompatible rivet having a head with a proximal end, a distal end and a central axis, the head having an internal passage extending from the proximal to the distal end of the head that is substantially parallel to the central axis of the head, the distal end of the head being mechanically connected to two or more legs that extend generally distally from the head and have an internal surface that faces the central axis, and (b) a bioabsorbable, biocompatible pin having radially flexible members extending to a distal end of the pin from a junction at a proximal end thereof, the pin being attached to and axially aligned with the rivet by an integral connection, such that axially-directed force shears the connection and drives the pin into the internal passage of the rivet to contact the internal surface of said legs and apply force on said legs in a direction perpendicular to the central axis for fixing the rivet in position.

12. The bioabsorbable biocompatible rivet and pin fastening device of claim 11 wherein the device is made from biocompatible aliphatic polyesters.

13. The bioabsorbable biocompatible rivet and pin fastening device of claim 12 wherein the absorbable polymeric matrix comprises an aliphatic polyester selected from the group consisting of polylactide, polyglycolide, poly-1,4-dioxan-2-one, polytrimethylene carbonate and poly($\epsilon$-caprolactone), copolymers and blends thereof.

14. The bioabsorbable biocompatible rivet and pin fastening device of claim 12 wherein the rivet contains a therapeutically effective amount of a therapeutic agent selected from the group consisting of antiinfectives, antiinflammatory agents, proteins, polysaccharides and combinations thereof.

15. The bioabsorbable biocompatible rivet and pin fastening device of claim 12 wherein the rivet contains a therapeutically effective amount of a therapeutic agent selected from the group consisting of analgesics hormones, bone regenerating growth factors, glycoproteins, lipoproteins and combinations thereof.

16. The bioabsorbable biocompatible rivet and pin fastening device of claim 12 wherein the pin contains a therapeutically effective amount of a therapeutic agent selected from the group consisting of antiinfectives, antiinflammatory agents, proteins, polysaccharides and combinations thereof.

17. The biabsorbable biocompatible rivet and pin fastening device of claim 12 wherein the pin contains a therapeutically effective amount of a therapeutic agent selected from the group consisting of analgesics hormones, bone regenerating growth factors, glycoproteins, lipoproteins and combinations thereof.

18. The bioabsorbable biocompatible rivet and pin fastening device of claim 11 wherein the aliphatic polyester is formed from a monomer selected from the group consisting of lactic acid, lactide (including L-, D-, meso and D,L mixtures), glycolic acid, glycolide, $\epsilon$-caprolactone, p-dioxanone (1,4-dioxan-2-one), trimethylene carbonate, 1,3-dioxan-2-one, p-dioxanone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof.

19. The bioabsorbable biocompatible rivet and pin fastening device of claim 11 wherein the pin has two or more members which are joined.

20. The bioabsorbable biocompatible rivet and pin fastening device of claim 11 wherein the pin has a circumferential notch and the rivet has an internal circumferential rib that may mate and lock the pin in the rivet.

21. The bioabsorbable biocompatible rivet and pin fastening device of claim 11 wherein at least one of the legs of the rivet has a lateral surface and one or more ribs thereon.

22. The bioabsorbable biocompatible rivet and pin fastening device of claim 11 wherein rivet and pin are linked by a detachable connection.

23. A bioabsorbable, biocompatible rivet and pin fastening device comprising:

(a) a bioabsorbable, biocompatible rivet having a head with a proximal end and a distal end and a central axis, the head having an internal passage extending from the proximal to the distal end of the head that is substantially parallel to the central axis of the head, the distal end of the head being mechanically connected to two or more legs that extend generally distally from the head and have an internal surface that faces the central axis, and (b) a bioabsorbable, biocompatible pin having a radially compressible members extending to a distal end of the pin from a junction at a proximal end thereof that are less compliant than the legs of the rivet and are adapted to be inserted into the internal passage of the rivet and which, as advanced from the proximal end toward the distal end of the head of the rivet, will contact the internal surface of said legs to apply force on said legs in a direction perpendicular to the central axis wherein the rivet is molded with the legs in substantially the position that the legs would be in with the pin in place.

* * * * *